United States Patent [19]

Fulcher

[11] Patent Number: 5,176,933
[45] Date of Patent: Jan. 5, 1993

[54] SUBSTITUTED SUCCINATE ESTERS AND LOW-CALORIE OILS CONTAINING THEM

[75] Inventor: John G. Fulcher, Dallas, Tex.

[73] Assignee: Recot, Inc., Plano, Tex.

[21] Appl. No.: 737,412

[22] Filed: Jul. 29, 1991

[51] Int. Cl.⁵ .............................................. A23L 1/01
[52] U.S. Cl. ................................... 426/531; 426/438; 426/520; 426/601; 426/611; 426/804; 560/190; 560/201
[58] Field of Search ................ 560/201, 190; 426/601, 426/611, 804, 531, 438, 520

[56] References Cited

U.S. PATENT DOCUMENTS

| | | |
|---|---|---|
| 2,161,213 | 6/1939 | Whitmore . |
| 4,470,421 | 9/1984 | Southwick ...................... 131/276 |
| 4,508,746 | 4/1985 | Hamm ................................ 426/601 |
| 4,582,927 | 4/1987 | Fulcher .............................. 560/201 |
| 4,673,581 | 6/1987 | Fulcher .............................. 426/531 |
| 4,830,787 | 5/1989 | Klemann .......................... 260/410 |
| 4,877,871 | 10/1989 | Klemann .......................... 536/124 |
| 4,888,195 | 12/1989 | Huhn ................................. 426/601 |
| 4,915,974 | 4/1990 | D'Amelia .......................... 426/611 |
| 4,927,658 | 5/1990 | Klemann .......................... 426/611 |
| 4,927,659 | 5/1990 | Klemann .......................... 426/611 |
| 4,956,478 | 9/1990 | Fakoukakis ...................... 549/255 |
| 4,959,465 | 9/1990 | Klemann .......................... 536/115 |
| 4,963,386 | 1/1990 | Klemann .......................... 426/611 |

OTHER PUBLICATIONS

Chemical Abstracts 73:109235p, 1970.

Primary Examiner—Joseph Golian
Assistant Examiner—Evan Federman
Attorney, Agent, or Firm—Rothwell, Figg, Ernst & Kurz

[57] ABSTRACT

Fatty alcohol succinic acid esters of the formula:

$$RCH=CH-CH_2-CH(COOR')CH_2(COOR'')$$

wherein R is a linear alkyl group of from 5 to 15 carbon atoms, R' and R" can be the same or different and are linear saturated, monounsaturated or diunsaturated alkyl groups of from 12 to 20 carbon atoms. These fatty alcohol esters can be prepared by reacting succinic anhydrides with long chain fatty alcohols, and have a low calorie value. The compounds are suitable for use in cooking oil compositions for the commercial production of reduced-calorie fried snack foods.

10 Claims, No Drawings

SUBSTITUTED SUCCINATE ESTERS AND LOW-CALORIE OILS CONTAINING THEM

BACKGROUND OF THE INVENTION

The present invention relates generally to synthetic substitutes for edible oils, such oils containing fatty alcohol esters. The chosen fatty alcohol esters have a low caloric value which makes them suitable for the commercial production of calorie-reduced fried snack foods. More particularly, the present invention is directed to low-calorie fatty alcohol esters of succinic acid and their use in low calorie cooking oil compositions.

Lipids (fats and oils) constitute between 30 and 40% of the caloric intake of the average American diet. Dietary fat, consisting of triglycerides, is digested to free fatty oils and monoglycerides primarily in the small intestine. The α-lipase steapsin cleaves the glycerol esters at the 1- and 3- positions. Fatty acids of 6 to 10 carbons and unsaturated fatty acids are rapidly absorbed, while those of 12 to 18 carbons are absorbed more slowly. Absorption of the β-monoglycerides by the mucosa of the small intestine results in a final digestion and absorption of up to 95% of the total dietary fat. Since fats yield about twice the energy per gram of either carbohydrates or proteins, substitution of a nondigestible material for a portion of the normal dietary fat offers an attractive and effective method for reducing total caloric intake and the control of obesity, hypertension, and other diseases associated with excessive caloric intake.

For successful commercial application, a material provided as a dietary fat substitute should be inexpensive, taste good, perform the processing functions of fat, have low calorie content (i.e. the material should be less than 40% absorbed), and must be safe for human consumption. To be inexpensive, the substitute materials should be under current manufacture, or synthesized from materials under current manufacture by a minimum number of processing steps.

Most of the current dietary fat substitutes are fatty acid esters, but fatty alcohol esters also are known. U.S. Pat. No. 4,508,746, issued to Hamm in 1985, describes long chain fatty alcohol esters of citric and tricarballylic acids. The citric acid esters lack thermal stability, however, and the tricarballylic acid starting material is not believed to be produced in commercial quantities.

U.S. Pat. Nos. 4,582,927, and 4,673,581, issued to Fulcher in 1986 and 1987, respectively, describe alkylmalonic and dialkylmalonic acid esters of long chain fatty alcohols, as well as their use in reduced calorie edible oils. These substituted malonic acids are not commercially available and their synthesis from diethyl malonate is relatively expensive at the current time.

U.S. Pat. No. 4,830,787, issued to Klemann et al. in 1989, describes hydroxysuccinic (malic) acid esters which contain both fatty acid and fatty alcohol esters. Despite low raw material cost, the product is expensive because separate esterification steps are required for the two ester types.

U.S. Pat. No. 4,888,195, issued to Huhn et al. in 1989, describes fatty alcohol esters of dicitrate ether, diisocitrate ether and citrate isocitrate ether and esters of polycarboxylic acid ethers containing 4 to 6 ester groups. The three step synthesis involved in the production of these compounds makes them cost prohibitive.

U.S. Pat. No. 4,959,465, issued to Klemann et al. in 1990, discloses succinate-extended sucrose which is further extended with hydroxyl-dicarboxylic acid esterified to two fatty alcohols. A minimum of three synthesis steps are required in preparing these compounds and the use of 3-hydroxyglutaric acid as a reaction substrate make these compounds prohibitively expensive.

Thus, there presently remains a need for inexpensive and stable synthetic substitutes for edible oils suitable for the commercial production of calorie-reduced fried snack foods.

SUMMARY OF THE INVENTION

The present invention overcomes this need in the industry by providing novel, inexpensive and stable fatty alcohol esters of succinic acid having the formula:

wherein R is a linear alkyl group of from 5 to 15 carbon atoms and R' and R" are the same or different and are linear saturated, monounsaturated or diunsaturated alkyl groups of from 12 to 20 carbon atoms.

The present invention additionally relates to low calorie cooking oil compositions comprising one or more fatty alcohol esters of succinic acid according to the above formula.

These fatty alcohol esters comprise synthetic oils and low melt solids that may be synthesized by a novel, inexpensive and simple method: Commercially available succinic anhydrides are reacted with long chain fatty alcohols in the presence of an organic acid catalyst, resulting in the formation of dialkyl alkenylsuccinates. These fatty alcohol esters have a low calorie value and are suitable for the commercial production of calorie-reduced fried snack foods. The presence of an alkenyl side chain advantageously provides low melting point, promotes oxidative stability and imparts good "mouthfeel" characteristics.

DETAILED DESCRIPTION OF THE INVENTION

In accordance with the present invention, the synthetic esters are represented by the formula:

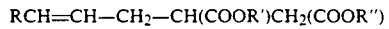

wherein R is a linear alkyl group of from 5 to 15 carbon atoms, e.g., pentyl, hexyl, heptyl, decyl, and the like; and R' and R" are the same or different and are linear saturated, monounsaturated or diunsaturated alkyl groups of from 12 to 20 carbon atoms, e.g., dodecyl, hexadecenyl, octadecenyl, lauryl, myristyl, palmityl, stearyl, oleyl, behenyl, linoleyl and the like.

In preferred succinate ester compounds, R is an alkyl group of from 11 to 15 carbon atoms and R' and R", are saturated alkyl groups of 16 or 18 carbon atoms (i.e. palmityl or stearyl) or monounsaturated or diunsaturated alkyl groups of 18 carbon atoms.

Esters which are particularly preferred for use as reduced calorie cooking oils are the dialkyl octadecenylsuccinate esters, such as dihexadecyl octadecenylsuccinate ester, dioleyl octadecenylsuccinate ester and the like.

The succinate ester compounds of this invention are synthetic organic compounds which display many of the desirable physical properties of animal fats and vegetable oils. They can be liquid, solid or semisolid at room temperature, depending upon their particular molecular weight and structure, and are liquids at normal cooking temperatures. Unlike naturally-occurring fats and oils, which are triglycerides (fatty acid esters of glycerol), the products of this invention can be derived from succinic anhydrides having the following formula:

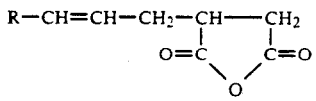

wherein R is a linear alkyl group of from 5 to 15 carbon atoms, and long chain fatty alcohols having the following formula:

R'—OH or R"—OH wherein R' and R" can be the same or different and are linear saturated, monounsaturated or diunsaturated alkyl groups of from 12 to 20 carbon atoms. Unlike triglycerides, these compounds resist hydrolysis by pancreatic lipase and other components of the digestive fluids present in the stomach and small intestine. As a result, most of the material is not absorbed by the small intestine. For example, from 0% to less than about 40% will be absorbed.

Examples of succinic anhydrides suitable for practicing this invention include octenyl, decenyl, dodecenyl, hexadecenyl, and octadecenyl succinic anhydrides. The alkenyl succinic anhydrides are prepared by reacting maleic anhydride with 1-alkenes at temperatures of from about 200° to about 250° C. These anhydrides also can be obtained commercially. They are manufactured in large quantity for use as plasticizers in alkyd resins and are relatively inexpensive. Examples of suitable 1-alkenes that can be used include 1-nonene, 1-decene and 1-dodecene. U.S. Pat. No. 4,956,478, issued to Fakoukakis et al. in 1990, discloses methods for preparing alkenyl succinic anhydrides and is incorporated herein by reference.

The synthesis of the succinate ester compounds of this invention can be accomplished by reacting one molar equivalent of the alkenyl succinic anhydride with two molar equivalents of a suitable long chain fatty alcohol in an organic solvent in the presence of an organic acid catalyst, such as p-toluenesulfonic acid or adipic acid. Examples of non-polar, inert organic solvents which can be used in the synthesis of the succinate ester compounds of this invention are toluene, benzene and the like.

The alkenyl succinic anhydride and fatty alcohol in organic solvent is refluxed for about 4 to about 6 hours. Typically, an organic solvent-water azeotrope forms which is collected in a trap. The resulting product is a dialkyl alkenylsuccinate having a low melting point, low caloric value and suitable as a synthetic substitute for edible oils. Dialkyl alkenylsuccinates can be prepared from alkenyl succinic anhydride by other methods, known to those skilled in the art.

Impurities can be removed from the dialkyl alkenylsuccinate formed by the above method by vacuum distillation and silica gel chromatography using conventional equipment and techniques familiar to those skilled in this field of chemistry.

The synthetic oils of the present invention also can comprise mixtures of the disclosed succinate esters with other, higher-calorie fats and/or oils. For example, the present succinate esters can be combined with (e.g. blended into) per se known cooking oil compositions based on vegetable and/or animal fats and/or oils.

Particularly preferred synthetic oils of the present invention have a melting point below 40° C., a boiling point above about 230° C., are absorbed by the small intestine of a mammal at a substantially lower rate than corn oil, and thus provide substantially fewer calories than corn oil when consumed by a mammal.

Food products fried in synthetic oils of the present invention will have a lower metabolic fat content than a similar product cooked in animal fat or vegetable oil. Similarly, food products in which the normal content of animal fat or vegetable oil has been partially or completely substituted by the synthetic oils of this invention have a lower metabolic fat content than similar products not containing synthetic oil.

The invention is further illustrated by the following examples, which are not intended to be limiting.

EXAMPLE I

Preparation of Dioleyl Octadecenylsuccinate

One molar equivalent of octadecenylsuccinic anhydride was added to a boiling flask (with attached Dean-Stark trap) containing a solution with two molar equivalents of oleyl alcohol in one liter of toluene. The mixture was refluxed and stirred for about 6 hours in the presence of the catalyst p-toluenesulfonic acid. Excess toluene was removed by distillation at ambient pressure and the residue was applied to a silica gel column. Elution with petroleum ether gave dioleyl octadecenylsuccinate. Oleyl alcohol and other impurities were retained on the column. The dioleyl octadecenylsuccinate has a low melting point and can be used for the commercial production of calorie-reduced fried snack foods.

EXAMPLE II

Preparation of Dihexadecyl Octadecenylsuccinate

One mole of octadecenylsuccinic anhydride (351 gm), 2.05 moles of hexadecanol (498 gm), 2.5 gm of adipic acid and one liter of toluene were combined in a boiling flask (with attached Dean-Stark trap) and refluxed for about 6 hours in the presence of the catalyst p-toluenesulfonic acid. Excess toluene was removed at ambient pressure. The residue was applied to a 200 gm silica gel column in 25 gm portions, and eluted with petroleum ether. Elution with petroleum ether gave dihexadecyl octadecenylsuccinate. Oleyl alcohol and other impurities were retained on the column. The dihexadecyl octadecenylsuccinate has a low melting point, is believed to have a greater oxidative stability than dioleyl octadecenylsuccinate of Example I, and can be used for the commercial production of calorie-reduced fried snack foods.

EXAMPLE III

Preparation of Dioleyl Tetradecenylsuccinate

Seventeen millimoles of tetradecenylsuccinic anhydride (5.0 gm), 34 millimoles of oleyl alcohol (9.1 gm), 50 mg of adipic acid and 10 ml of toluene were combined in a boiling flask (with attached Dean-Stark trap) and refluxed for about 6 hours in the presence of the catalyst p-toluenesulfonic acid. Excess toluene was removed at ambient pressure. The residue was applied to a silica gel column, and eluted with petroleum ether. Elution with petroleum ether gave dioleyl tetradecenylsuccinate. Oleyl alcohol and other impurities were retained on the column. The dioleyl tetradecenylsuccinate has a low melting point and can be used for the commercial production of calorie-reduced fried snack foods.

EXAMPLE IV

Synthetic Oil Absorption Studies in Fischer 344 Rats

The objective of this experiment was to determine whether dialkyl alkenylsuccinates, such as dihexadecyl octadecenylsuccinate, are poorly absorbed in mammals and thus are suitable for use as low calorie cooking oils. Thus, it is preferred that a synthetic oil be minimally absorbed by an animal to reduce any possibility of toxic effects. Eighty male and eighty female Fischer 344 rats, 4 to 6 weeks old and weighing about 80-100 gm each, were obtained from Charles River (Kingston, R.I). The male rats were fed Harlan Industries TEKLED Rodent Chow for four days while the female rats were fed TEKLED chow for seven days. On the fifth day, the male and female rats were randomly assigned to different groups of five. Groups 1 through 16 were male rats, and groups 17 through 32 were female rats. Also on the fifth day, the diet of the male rats was changed from TEKLED to Purina Basal Purified Diet containing 10% corn oil (control diet). The diet of the female rats was changed from TEKLED to Purina Basal Purified Diet containing 10% corn oil (control diet) on the eighth day of the experiment. After each group of rats had been fed on the Purina Basal Purified Diet containing 10% corn oil for seven days, the diet of 30 groups out of the 32 groups of rats was changed. One group of 5 males and one group of 5 females remained on the 10% corn oil diet throughout the entire experiment. The remaining groups of male and female rats were fed Purina Basal Purified Diet with 7.5% corn oil plus a varying amount of a synthetic oil on a daily basis for two weeks. Thus, one group of 5 male and 5 female rats were fed daily on Purina Basal Purified Diet with 7.5% corn oil plus 2.5%, 5.0% or 7.5% of dialkyl alkenylsuccinate (DAS), i.e, dihexadecyl octadecenylsuccinate.

Fecal samples were collected from the male and female control rats and the low dose (2.5%) synthetic oil fed rats on a daily basis for seven days starting in the second week of the synthetic oil diet. The feces were stored in a freezer until all samples had been collected by the seventh day. The feces were then analyzed for their content of synthetic oils using Soxhlet oil analysis. The samples for each group were combined and ground using a blender, taking care to pulse on and off to avoid separating the synthetic oil from the samples. Samples of the blended feces ranging from about 2-4 grams were placed in separate 25 × 80 mm cellulose extraction thimbles (Whatman Cat. #2800 258) of known weight and the thimbles with the fecal matter were each weighed. Each thimble was placed into the extraction holder of a separate 125 ml Soxhlet flask of known weight and containing about 100 ml of chloroform and 2-3 boiling chips. Each apparatus was assembled on a hot plate with water passing through the condensers. The oils were extracted from the feces by refluxing for about 16-20 hours. The temperature of the hot plate was adjusted such that the extraction chambers emptied about ten times per hour. Each thimble was removed from the extraction chamber, and the flask was then reheated to reflux most of the chloroform into the thimble chamber. When the thimble chamber was about full, the flask was removed from the hot plate, and the chloroform was poured into a waste container until about 20-30 ml of residue were left in the bottom of each flask. The temperature of each flask was reduced by lowering the heat setting on each hot plate (low-3 setting on Corning hot plate), and residual chloroform was evaporated under a flush of nitrogen.

Each flask with residue was allowed to cool to room temperature and weighed. The amount of synthetic oil in each sample was calculated using the following equation:

$$\% \text{ Oil} = \frac{(\text{Oil} + \text{Flask Tare Wt.}) - (\text{Flask Tare Wt.})}{(\text{Sample} + \text{Thimble Tare Wt.}) - (\text{Thimble Tare Wt.})} \times 100$$

DAS was minimally absorbed by the rats. The male animals absorbed on average 14 percent of the dietary DAS and the female animals absorbed 13 percent.

We claim:

1. A method for preparing calorie-reduced snack foods comprising cooking a snack food in an edible oil comprising one or more compounds for the formula:

RCH=CH—CH$_2$—CH(COOR')CH$_2$(COOR")

wherein R is a linear alkyl group of from 5 to 15 carbon atoms, R' and R" can be the same or different and are linear alkyl or monounsaturated or diunsaturated alkenyl groups of from 12 to 20 carbon atoms.

2. The method according to claim 1, wherein R is a linear alkyl group of from 11 to 15 carbon atoms, R' and R" are the same or different and are linear alkyl or monounsaturated or diunsaturated alkenyl groups of 16 to 18 carbon atoms.

3. The method according to claim 2, wherein the edible oil comprises dihexadecyl octadecenylsuccinate.

4. The method according to claim 2, wherein the edible oil comprises dioleyl octadecenylsuccinate.

5. The method according to claim 2, wherein the edible oil comprises dioleyl tetradecenylsuccinate.

6. A calorie-reduced snack food prepared by the process of claim 1.

7. A calorie-reduced snack food prepared by the process of claim 2.

8. A calorie-reduced snack food prepared by the process of claim 3.

9. A calorie-reduced snack food prepared by the process of claim 4.

10. A calorie-reduced snack food prepared by the process of claim 5.